United States Patent [19]

Dahlberg et al.

[11] 4,356,383
[45] Oct. 26, 1982

[54] THERMOSTATICALLY CONTROLLED ELECTRIC FLUID HEATING APPARATUS

[75] Inventors: Bengt A. G. Dahlberg, Lund; Bengt M. Holmberg, Bjarred; Lennart O. E. Nilsson, Genarp, all of Sweden

[73] Assignee: Gambro AB, Sweden

[21] Appl. No.: 96,001

[22] Filed: Nov. 20, 1979

[30] Foreign Application Priority Data

Nov. 22, 1978 [SE] Sweden .............................. 7812016

[51] Int. Cl.³ ..................... H05B 1/02; B67D 5/62; A61F 7/00; F24H 1/12
[52] U.S. Cl. .............................. 219/308; 128/214 A; 128/399; 137/341; 165/46; 219/299; 219/302; 219/305; 219/328; 219/330; 219/524; 222/146 HE
[58] Field of Search ............. 219/296, 299, 301, 302, 219/305, 308, 525, 524, 214, 330, 328; 128/214 A, 399; 165/46; 137/341; 222/146 R, 146 HE

[56] References Cited

U.S. PATENT DOCUMENTS

| | | | |
|---|---|---|---|
| 1,794,215 | 2/1931 | Titus | 128/214 A |
| 3,140,716 | 7/1964 | Harrison et al. | 128/214 A |
| 3,443,060 | 5/1969 | Smith | 219/302 |
| 3,475,590 | 10/1969 | Pins | 219/302 |
| 3,485,245 | 12/1969 | Lahr | 219/302 X |
| 3,590,215 | 6/1971 | Anderson et al. | 128/214 A |
| 4,019,020 | 4/1977 | Bilbee et al. | 219/302 |
| 4,167,663 | 9/1979 | Granzow et al. | 128/214 A |

FOREIGN PATENT DOCUMENTS

| | | | |
|---|---|---|---|
| 2330410 | 6/1977 | France | 219/308 |
| 2331230 | 6/1977 | France | 219/308 |
| 2405610 | 6/1979 | France | 219/302 |

Primary Examiner—A. Bartis
Attorney, Agent, or Firm—Lerner, David, Littenberg & Samuel

[57] ABSTRACT

Heating apparatus for heating of a fluid. The heating apparatus comprises a conduit having a fluid passage therethrough for conduction of a fluid to be heated, a heating device, such as for example electrical heating plates, in heat transfer contact with a portion of the conduit for heating the fluid being conducted therethrough, and a temperature sensing device positioned in engagement with the conduit at a predetermined location along the conduit external to the conduit for sensing the temperature of the fluid to be conducted therepast. A contact member is arranged to engage the flexible conduit at the predetermined location for compressing the flexible conduit to constrict the cross sectional area of the flow passage thereat when the flow rate of the fluid is below a predetermined flow rate. Preferably, the contact member is spring biased towards the flow passage constricting position, and is movable away from such position when the flow rate exceeds a predetermined flow rate. In this manner, the fluid in the conduit is maintained in temperature sensing relationship with the temperature sensing device.

17 Claims, 7 Drawing Figures

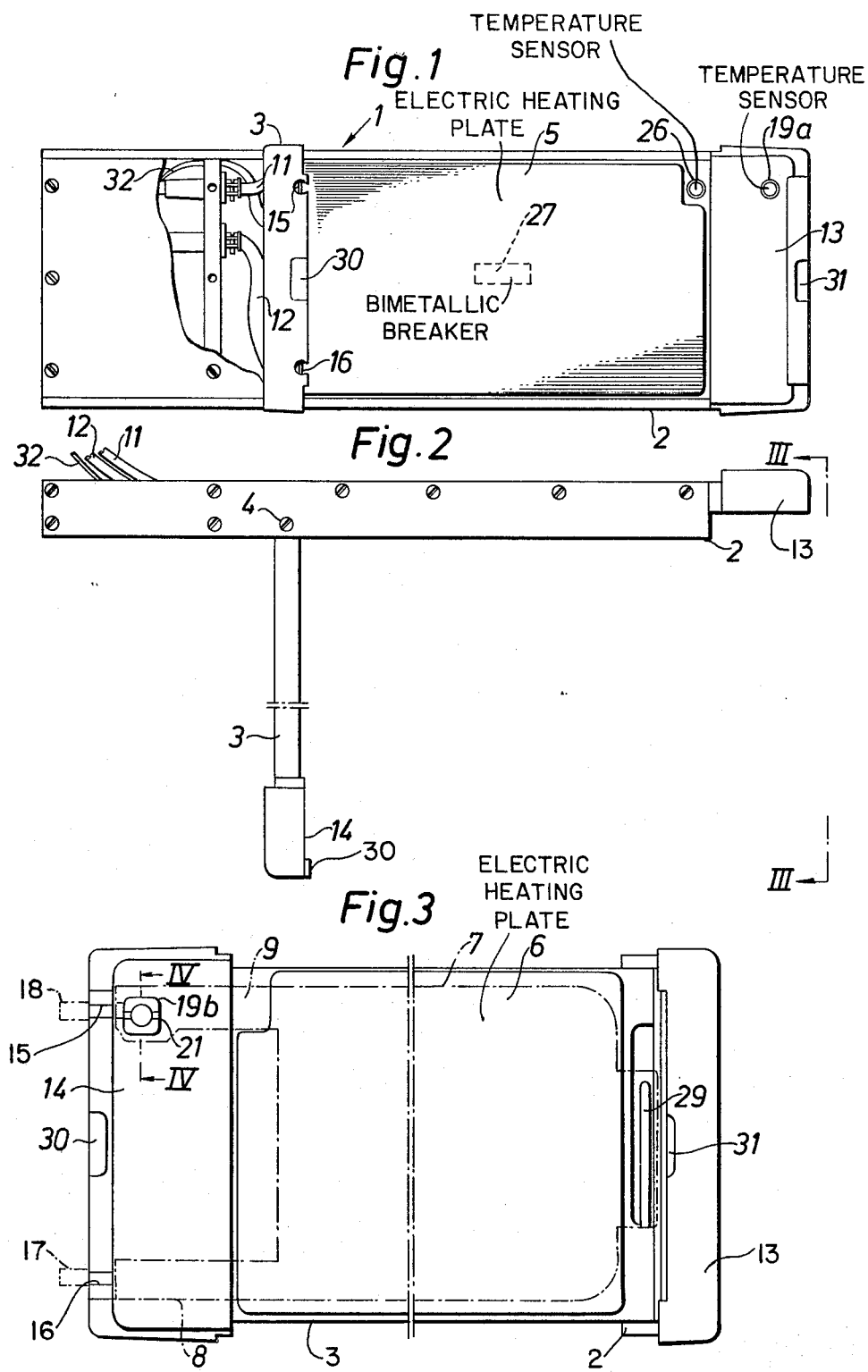

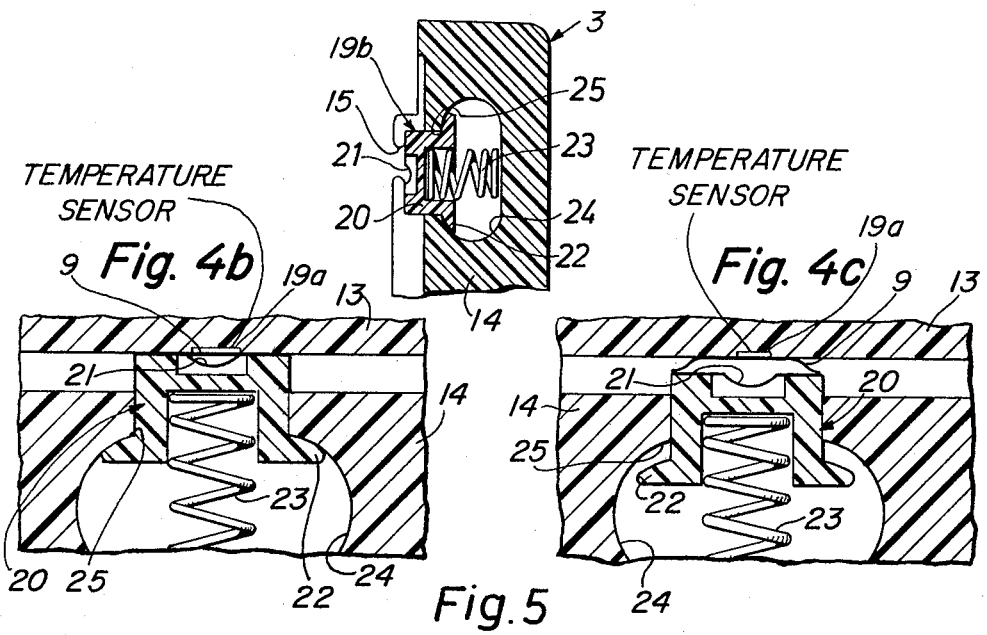
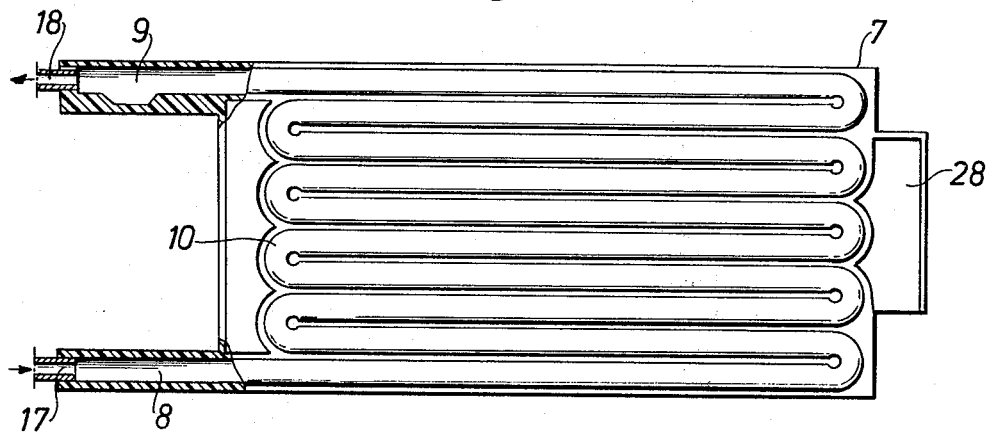

THERMOSTATICALLY CONTROLLED ELECTRIC FLUID HEATING APPARATUS

BACKGROUND OF THE INVENTION

The present invention relates to a heating apparatus for heating of a fluid flowing in a conduit, and more particularly to a heating apparatus in combination with means for measuring and monitoring the temperature of the heated fluid. The heating means for heating of the fluid may comprise any suitable means, for example conventional electrical means such as electrical heating plates, coils or the like, which are arranged in heat transferring contact with at least a part of the conduit.

As used herein, the term "fluid" is intended to cover liquids as well as gases.

One prior art heating device of the above-mentioned kind is known, for example, from German Offenlegunschrift No. 2,802,993. In particular, this known device comprises a bag member provided with fluid passages therethrough for conduction of the fluid. The bag is adapted to be located between electrical heating plates, and comprises an outlet and an inlet in fluid communication with such flow passages. Further, there are provided two temperature transmitters, one of which is provided at the outlet for measuring the temperature of the outflowing (or heated) fluid, and the other of which is provided at the inlet for measuring the inflowing (or unheated) fluid. On the basis of these measured temperatures, the current supplied to the heating plates is controlled through the use of a suitable controlling system.

One serious disadvantage of this known device is however that the temperature transmitters are provided in intimate contact with the heating plates, enclosed within the same cover or box with the conduit or bag, without significant insulation to radiant and/or conductive heat from the heating plates.

Furthermore, since the temperature transmitters necessarily must be sensitive to temperature fluctuations, any instantaneous increase or decrease in the temperature, either involuntarily through direct influence from the heating plates, or through actual temperature fluctuations of the fluid, is immediately sensed by the temperature transmitters. As can be appreciated, the risk of inaccurate controlling may thus result.

Another disadvantage of the known device is that the fluid passages in the bag have the same cross-sectional area along their entire lengths. This is of particular concern at those locations where the fluid is conducted past the temperature transmitters when the fluid is flowing at lower rates of flow. In this instance, the fluid tends to distribute evenly across the entire width of the passage in the form of a thin layer. As a consequence, at such low rates of flow, the fluid may be pushed aside by the temperature transmitter in contact with the conduit so that it will flow in a path around the temperature transmitter rather than in intimate contact with same at the measuring point. The temperature transmitter will thus sense the surface temperature of the bag at this point rather than being in close contact with the flowing fluid to sense the temperature of the fluid. Accordingly, the temperature transmitters may indirectly control the current supplied to the heating plates on the basis of a temperature other than that of the fluid which it is desired to measure.

These and other disadvantages of the prior art are overcome with the heating device of the present invention.

SUMMARY OF THE INVENTION

In accordance with the present invention there is provided a heating apparatus for heating of a fluid which comprises a conduit having a fluid passage therethrough for conduction of a fluid to be heated, heating means in heat transfer contact with a portion of the conduit for heating the fluid being conducted therethrough, and temperature sensing means positioned at a predetermined location along the conduit external to the conduit for sensing the temperature of the fluid to be conducted through the conduit. Flow maintenance means associated with the conduit are provided for maintaining the fluid in the fluid passage of the conduit in contact with the conduit at the predetermined location when the flow rate of the fluid is below a predetermined flow rate so as to guide and maintain the fluid in the conduit in temperature sensing relationship with the temperature sensing means. In this way, even at low rates of flow, the fluid will be concentrated to the fluid passage in close contact with the temperature sensing means.

In the preferred embodiment, the flow maintenance means comprises constricting means for constricting the cross-sectional area of the fluid passage at the predetermined location to a predetermined cross-sectional area in relation to the cross-sectional area of the fluid passage in the portion of the conduit in heat transfer contact with the heating means. Preferably, this constricting means is responsive to the flow rate of fluid through the fluid passage at the predetermined location to vary the cross-sectional area of the fluid passage between the predetermined cross-sectional area when the flow rate of the fluid is below a predetermined flow rate and a larger cross sectional area when the flow rate of the fluid is above a predetermined flow rate.

More preferably, the conduit comprises a flexible conduit and the constricting means comprises contact means engagable with the flexible conduit at the predetermined location for compressing the flexible conduit to restrict the cross-sectional area of the fluid passage to the predetermined cross-sectional area when the flow rate of the fluid is below the predetermined flow rate. The contact means preferably includes at least one groove therein into which a portion of the flexible conduit at the predetermined location is forced to define the predetermined cross-sectional area of the fluid passage. Still more preferably, the contact means comprises a contact member movable between a contact position in which the contact member engages the flexible conduit to constrict the cross-sectional area of the flow passage to the predetermined cross-sectional area, and a second position in which the cross-sectional area of the flow passage is larger than the predetermined cross-sectional area, and biasing means for normally urging the contact member towards the contact position. The contact member is movable towards the second position in response to the flow rate of the fluid in the flow passage being of a value greater than the predetermined flow rate.

In this way, when the fluid flows through the flow passage past the location of the temperature transmitter at a relatively low flow rate below the predetermined flow rate, the cross-sectional area of the flow passage will be constricted so as to ensure that the fluid is in contact with the conduit at the predetermined location so as to be in accurate temperature sensing relationship with respect to the temperature sensing means. However, when the flow rate of the fluid increases, and is above the predetermined flow rate, the fluid passage at the location of the temperature sensing means is expanded to allow a larger amound of fluid to pass per unit time at the increased flow rate, while still maintaining the fluid in contact with the conduit to maintain the accurate temperature sensing relationship between the temperature sensing means and the fluid.

According to another aspect of the present invention, there is provided a fluid conduit for use in an apparatus for heating and monitoring fluid conducted through the fluid conduit, the apparatus including heating means adapted to be arranged in heat transfer contact with a portion of the fluid conduit and temperature sensing means adapted to be positioned in temperature sensing relationship external to the fluid conduit for sensing the temperature of the fluid being conducted therethrough. The fluid conduit comprises a plastic bag having a first section defining at least one fluid passage therethrough and being adapted to be arranged in heat transfer contact with the heat transfer means, and a first channel section being spaced from the first section and in fluid communication with the at least one fluid passage in the first section, the first channel section also being adapted for positioning in temperature sensing relationship with the temperature sensing means. Also a second channel section is preferably provided in fluid communication with the fluid passage in the first section for introducing fluid into the fluid passage of the first section to be heated by the heating means, the second channel section also being spaced from the first section. Still further the first section preferably comprises a plurality of longitudinally extending flow channels arranged in side-by-side relationship and communicating with one another to define a laterally extended heat transfer surface for arrangement in heat transfer contact with the heating means, and the first and second channel sections are laterally spaced from the laterally extending heat transfer surface so as to be insulated from the heating means when the bag is placed in heat transfer contact therewith.

These and further features and characteristics of the present invention will be apparent from the following detailed description in which reference is made to the enclosed drawings which illustrate a preferred embodiment of the present invention.

BRIEF DESCRIPTION OF THE DRAWINGS

FIG. 1 is a side elevational view of the heating apparatus in accordance with the present invention, showing a containing member enclosure therefor in the open position.

FIG. 2 is a plan view of the heating apparatus of FIG. 1.

FIG. 3 is a end elevational view of the heating apparatus in accordance with the present invention, taken along lines III—III of FIG. 2.

FIG. 4a is a sectional view of a portion of the heating apparatus in accordance with the present invention, taken along lines IV—IV off FIG. 3 to illustrate the contact means in accordance with the present invention.

FIGS. 4b and 4c are sectional views, similar to FIG. 4a, illustrating a portion of the heating apparatus when the box member and cap member are closed, FIG. 4b illustrating the relationship between the contact means, the outlet channel and the temperature sensor when there is a relatively low rate of flow through the outlet channel, whereas FIG. 4c illustrates the relationship of such components when there is a relatively high rate of flow.

FIG. 5 is a plan view of a plastic bag conduit in accordance with the present invention which is adapted to be used with the heating apparatus in accordance with FIGS. 1-4.

DETAILED DESCRIPTION OF THE PREFERRED EMBODIMENT

As the present invention is primarily intended for use in heating of infusate, such as for example blood, it will be described in connection therewith. However, it should be noted that the present invention is not intended to be restricted to only this field of application, but could be used for heating of other fluids, both liquids as well as gases for simultaneous control and monitoring of the temperature thereof.

Referring now to the drawings in which like reference characters represent like elements, there is shown in FIGS. 1 and 2 the heating apparatus in accordance with the present invention, generally designated 1. The heating apparatus 1 generally comprises a rectangular box-shaped member 2 having a rectangular enclosure member or cap 3. The box member 2, as well as the cap member 3 are preferably made of a suitable plastic material. The cap member 3 is pivotally mounted to the box member 2, as shown at 4, so as to be pivotally openable and closable.

For heating purposes, the box member 2 and cap member 3 are each provided with suitable heating elements. Specifically, the inside of the box member 2 is recessed and provided with a laterally extending aluminum heating plate 5 which substantially covers the entire recessed surface within the box 2, while the inside of the cap member 3 is correspondingly recessed and provided with a second aluminum heating plate 6 which substantially covers the recessed surface of the interior of the cap member 3. The recessed portions and the heating plates 5, 6 are positioned so that the two heating plates 5, 6 will be spaced apart and face one another when the cover 3 is in its closed position. The aluminum plates 5 and 6 preferably comprise relatively thin plates having a thickness on the order of 0.5 millimeters so as to maintain the residual or rest heat in the plates as low as possible. Additionally, the plates are conveniently grounded in a suitable manner and fitted with suitable means for protection against overheating, as will be described more fully hereinbelow.

The two plates 5 and 6 on the interior of the box 2 and the cap 3 are adapted to abut opposing sides of the suitable conduit or bag 7 which is designed to be placed therebetween (see FIGS. 3 and 5) for heating of an infusate which is caused to flow through flow passages of the bag in a manner to be more fully described hereinbelow. For heating purposes, heating foils in the form of coils are attached to the back of each of the aluminum plates 5 and 6, which coils are supplied with current by lines 11 and 12 connected externally to a source of current, not shown. The current supplied heating coils, may thus be electrically heated to in turn heat the two aluminum plates 5 and 6. Between the aluminum plates 5 and 6 and the inside of the cap and box 2 and 3, respectively, there may be provided a suitable thermal insulating material (not shown), such as for example polyurethane foam insulation.

As is shown in the drawings, the box 2 as well as the cap 3 are provided with respective inlet/outlet parts or members 13, 14 integrally formed with the box 2 and cap 3 at one end thereof. The aluminum plates 5 and 6 do not extend over or cover the two inlet/outlet parts 13 and 14, and thus the parts 13 and 14 form together an air pocket which is shielded from the remaining portion of the apparatus 1 when the box 2 is closed by the cover 3.

A temperature transmitter 19a, as shown in FIG. 1, is provided in the upper right hand corner of the inlet/outlet part 13 on the box member 2. In a similar manner, contact means 19b (see FIG. 3) is provided in the upper left hand corner of the inlet/outlet part 14 on the cover 3. In this manner, the bulb of the temperature transmitter 19a is adapted to be in opposing relationship to the contact means 19b when the box 2 is closed with the cover 3. It will be appreciated that this temperature transmitter 19a is insulated from the heating plates 5 and 6 through the air pocket formed by the inlet/outlet parts 13 and 14 on the box 2 and cover 3 at the end of the heating device 1, i.e., by virtue of its spacing from the heating zone. Of course, it should be appreciated that insulation from radiant and/or conductive heat generated in the heating zone may also be provided in another suitable manner, such as through the use of thermal insulation which may be placed to surround the area of the temperature transmitter or sensing means 19a and to shield such area from the heating means 5, 6.

The contact means 19b is more fully shown in detail in FIGS. 4a-4c. This contact means 19b comprises a generally square shaped button 20 disposed in alignment with and spaced from the circular recess 15 provided in the cover member 3. On its outer surface, i.e., facing away from the cover member 3, the square button 20 is provided with a centrally located groove 21, and on its inner surface there is provided a peripheral upstanding flange 22 for mounting of the square button 20 in a recess or cavity 24 in the inlet/outlet part 14 of the cover 3. The groove or notch 21 in the button 20 is adapted to receive a portion of the outlet channel q of the plastic conduit bag 7, as is more fully described hereinbelow. A suitable biasing means, such as for example a spring 23 is provided for biasing the contact button 20 outwardly away from the recess or cavity 24, i.e., away from the surface of the inlet/outlet part 14 adapted to mate with the inlet/outlet part 13 on the box 2. In this regard, the spring 23 is appropriately received in the cavity 24 of the inlet/outlet part 14 and between the button 20 and the back wall of the cavity 24. The contact button 20 is retained against the action of the spring 23 in the cavity 24 through the cooperation between the flange 22 thereof and a corresponding edge 25 of the cavity 24. As can be appreciated, the contact button 20 may be moved against the spring 23 to move further into the cavity 24.

The conduit 7 which is particularly adapted for use with the heating device 1 comprises a flexible plastic bag member 7 which is more fully shown in FIG. 5. In this regard, it is to be noted that the bag 7 shown in FIG. 5 differs slightly from the bag schematically shown in FIG. 3. For instance, the bag schematically shown in FIG. 3 comprises rounded corners, while the bag of FIG. 5 is provided with relatively sharp corners. Additionally, the shape of the outlet channel 9 is slightly different. Fundamentally, however, the two bags do not differ from each other.

The bag 7 comprises an inlet channel 8 and an outlet channel 9, with a flow passage 10 being defined therebetween. The plastic bag may be made from a suitable plastic material such as for example polyvinyl chloride (PVC) and preferably has substantially thin walls defining the fluid passage 10 so that heat generated by the aluminum plates 5 and 6 will serve to heat the fluid flowing through the fluid passage 10. The flow passage 10 in the preferred embodiment comprises a series of longitudinally extending channels which are interconnected to one another at the ends thereof to provide a zig-zag or serpentine type path of flow between the channels 8 and 9, and forms together therewith an uninterrupted flow passage for the infusate. Essentially, the channel portion 10 of the conduit 7 provides or defines a laterally extending heat transfer section of a suitable width and length corresponding to the width and length of the aluminum plates 5 and 6 for heating the infusate or blood as it is conducted through the flow passage 10. Such an extended section provides a sufficient area for adequate heating of the fluid being conducted in the flow passage 10 when the bag 7 is placed in the device 1, the fluid passage 10 will be completely surrounded by the aluminum heating plates 5 and 6.

As can be seen from FIG. 5, the inlet channel 8 as well as the outlet channel 9 extend laterally from the fluid passage 10 to form essentially straight extensions of the bag 7. These channels 8 and 9 are adapted to be located completely within the air pockets defined between the inlet/outlet parts 13 and 14 when the box 2 is closed by the cover 3, so as to be essentially insulated from the heat generated in the heating zone by the heating plates 5 and 6. Thus, the fluid will be conducted from the inlet channel 8 into the fluid channels of the fluid passage 10 of the bag 7 and from there into the common outlet 9. The heating of the fluid will only occur in the flow passage 10 between the inlet and outlet channels 8, 9.

The inlet channel 8 is connected to a suitable supply conduit 17 while the outlet channel 9 is in turn connected to a suitable withdrawal conduit 18. The conduits 17 and 18 deliver and withdraw infusate to and from the bag 7 respectively. The inlet/outlet part 14 of the cap 3 is provided with two essentially circular recesses 15 and 16 in the end thereof forming essentially round openings providing a passage into the interior of the device 1. These openings 15 and 16 are adapted to receive and retain by means of a suitable snap locking mechanism the conduits 17 and 18 connected to the bag 7 through which the infusate is adapted to be conducted. Thus, the lines 17 and 18 serve to keep the bag 7 in place in the device 1.

The outlet channel 9 is provided with an enlarged section in comparison to the inlet channel 8, which, as can be seen in FIGS. 3, 4b and 4c will essentially cover the outer surface of the contact means 19b, and in particular the entire contact button 20. The contact means 19b, in combination with the spring 23 and the temperature transmitter 19a will thereby lock the bag 7 in position when the box 2 is closed with the cover member 3. By virtue of this locking between the contact means 19b and the temperature transmitter 19a, the flexible outlet channel 9 will be compressed to constrict the cross-sectional area of the channel in the vicinity of the temperature transmitter 19a. Specifically, flow will be concentrated to flow through the portion of the outlet channel 9 which is pressed into the groove 21 in close contact with the bulb of the temperature transmitter 19a whereby the fluid flowing through the outlet channel 9 will be in intimate or close contact with the temperature transmitter 19 and thus in suitable and accurate temperature sensing relationship to provide an accurate measurement of the temperature of the fluid flowing therethrough. That is, the outlet channel 9, by virtue of its flexibility and confinement between the contact means 19b and the temperature transmitter 19a will be compressed to provide a relatively small opening or channel within the internal part of the outlet channel 9, as defined by the groove 21 in the contact means 19b.

By virtue of the spring biasing force exerted on the contact member of the spring 23, at higher rates of flow, the contact means 19b will be pressed against the action of the spring 23 inwardly into the recess cavity 24 so that a larger amount of infusate per unit time can be conducted past the temperature transmitter 19a. At the same time, however, because of the higher rates of flow, the fluid flowing past the temperature transmitter 19a will still be in intimate and close contact with the temperature transmitter 19a. Thus, it will be appreciated that the components are expandable to allow a larger flow passage, and thus a larger amount of fluid to pass per unit time when the flow rate of the fluid through the outlet channel 9 is at a higher rate. As can be appreciated the amount of expansion of the flow passage past the temperature transmitter 19a is dependent on the flow rate of the fluid, with a smaller cross-sectional area being provided for lower flow rates and a larger cross-sectional area being provided for larger flow rates.

Preferably, a second temperature transmitter 26 (see FIG. 1) is also provided in the box 2 near the inlet/outlet part 13. However, it is to be noted that no contact means is provided for the second temperature transmitter 26. As is shown in FIG. 1, the two temperature transmitters 19a and 26 are in line with each other, with the temperature transmitter 26 being located innermost and carried by the box member 2. The two temperature transmitters 19a and 26 are connected to a suitable system (not shown) through lines 32 to control the current supply to the aluminum plates 5 and 6, in dependence on the measured temperature of the infusate. Thus, if the temperature exceeds a certain specified temperature, the current supplied to aluminum plates 5 and 6 will be decreased to lower the temperature thereof whereas if the temperature is below a desired temperature, the current supply may be increased.

As is apparent from the foregoing, the temperature transmitter 19a measures the temperature of the infusate which leaves the device 1, while the temperature transmitter 26 is primarily adapted to interrupt the current supply to the aluminum plates 5 and 6 when the temperature of the infusate exceeds a specified predetermined temperature. For example, when the infusate is blood, such temperature for the temperature transmitter 26 may for example be 42° C. so that if the temperature of the infusate exceeds 42° C., the current supplied to the aluminum plates 5 and 6 will be immediately terminated. The temperature transmitter 26 thus serves as an extra safety protection against overheating of infusate. In this regard, the requirement of quick action with respect to the monitoring transmitter 26 is not so great as with the temperature transmitter 19a; however, the monitoring transmitter 26 should guarantee that the current supplied to the heating elements or plates 5 and 6 is interrupted when the temperature of the fluid exceeds a predetermined higher most value in comparison to the uppermost limit of the desired temperature sensed by the temperature transmitter 19a.

A further protection against overheating comprises a pair of bimetallic breakers (bimetallic breaker 27 being shown in FIG. 1) one on each side of the respective back sides of the aluminum plates 5 and 6, which are adapted to interrupt the current supplied to the plates when the temperature thereof exceeds a predetermined temperature, such as for example, 75° C. when the device 1 is being used to heat infusate such as blood. Thus, the bimetallic breakers 27 serve to prevent overheating of the plates 5 and 6, as well as the consequent overheating of fluid flowing through the conduit bag 7. Such overheating of the plates 5 and 6 may occur for instance when the device 1 is not connected with a bag 7 or when fluid is not flowing therethrough.

For controlling the temperature of the device 1, suitable means are provided, such as for example a computer, which is adapted to control the set temperatures, as well as the measured temperatures and to control the supply of current on the basis thereof. Furthermore, it will be appreciated that the computer or other suitable control devices may be dependent on the flow rate of the fluid flowing therethrough. Still further, the control device may be connected to a suitable alarm system if desired.

When the plastic bag 7 is placed in the device 1, it is important that the bag be positioned in the position shown in broken lines in FIG. 3. In this regard, it is convenient to locate the bag in a generally vertical position in the present device 1 with the inlet channel 8 being located beneath the outlet channel 9 so that the fluid during the heating will flow in a direction against gravitational influences. One reason for this is that the fluid flow out of the heating device into the outlet conduit 18 can be immediately interrupted, such as for example if the measured temperature is too high. On the other hand, if the fluid were flowing in a direction influenced by gravitation, i.e., if the fluid were introduced at an uppermost elevation and conducted downwardly to the outlet, and if the temperature measured were too high and the fluid flow interrupted, the amount of fluid at the level above the outlet channel might flow out of the device 1 due to gravitation. This may be particularly serious if the fluid comprises an infusate such as blood which is to be introduced into a patient after having been heated with the heating device 1.

Accordingly, in the preferred embodiment, a rod, such as rod 29 (see FIG. 3) is provided in the cap 3 which, in cooperation with a rod receiving pocket or recess 28 of the bag 7, permits insertion of the bag in only one direction so that the outlet channel 9 having the enlarged width will always be located vertically above the inlet channel 8 and thus positioned over the contact means 19b. With such an arrangement, if the bag is turned around or upside down, the entrance into the pocket 28 will be facing away from the rod 29 and it will be impossible to attach the bag 7 in the device 1. In this way, the bag will always be correctly positioned in the device 1.

To facilitate the opening and closing respectively of the box 2 and the cap 3, a handle in the form of finger grips 30, 31 is provided on the cap 3 and the box 2.

With respect to the use of the present device, as noted above, this device is particularly useful in controlling heating of a fluid such as an infusate, for example blood, which is to be introduced into a patient. According to the present invention, the infusate is adapted to flow through a flow passage 10 in the bag 7 of the device 1 which are located in a heating zone of the device 1 whereby the temperature of the heated infusate is to be monitored and controlled so as not to exceed 42° C. If the temperature for any reason exceeds 42° C., a control system is activated to interrupt the current supply to the heating plates 5 and 6 of the device. If on the contrary, the temperature falls essentially below 37° C., this control system will similarly be activated whereby the current supplied to the heating plates will be increased. At overheating, such as 75° C. of the heating plates, the current supply will also be interrupted through the use of bimetallic breakers 27 which are adapted to sense the temperature of the heating plates. The present device is intended for use in heating of infusates of about 15° C. to a minimim of about 40° C. at a temperature allowance of plus and minus 0.5° C., and at flows of from 15 to 150 ml per minute.

Accordingly, as is seen in accordance with the present invention, there is provided a heating apparatus 1 for heating of a fluid. The heating apparatus 1 includes a conduit or bag 7 through which fluid to be heated is conducted. The heating apparatus 1 also includes suitable heating means, such as aluminum heating plates 5, 6 which are electrically heated and which are arranged in heat transfer contact with a portion of the bag 7 through which the fluid flows. A temperature sensing means or transmitter 19a is provided located externally to the bag 7 at a predetermined location therealong for sensing the temperature of the fluid flowing therepast. Flow maintenance means are provided for maintaining the flow of fluid in the fluid passage at which the temperature sensing means 19a is position so as to maintain the fluid in contact with the conduit to provide for accurate temperature sensing relationship between the temperature sensing means 19a and the fluid flowing in the bag 7 when the flow of fluid is below a predetermined flow rate. In the preferred embodiment, the flow maintenance means comprises means for constricting the cross-sectional area of the flow passage at the predetermined location to a cross-sectional area which is less than the cross-sectional area of the flow passage 10 in a portion of the bag 7 in heat transfer contact with the heating means 5, 6. Preferably, the flow constricting means is variable to vary the cross-sectional area at the predetermined location in response to the flow rate of the fluid therepast.

The particular constricting means comprises in the preferred embodiment a spring biased contact button 20 having a groove 21 therein for constricting or compressing the flexible outlet channel 9 at a predetermined location to constrict the cross-sectional area of the flow passage to define a predetermined cross-sectional area of the flow passage thereat when the flow rate of the fluid is below the predetermined flow rate. The contact button 20 is biased in a direction to constrict the flow passage to the predetermined cross-sectional area and is movable away therefrom in response to flow rates in the flow passage being at a value greater than the predetermined flow rate to enlarge the cross-sectional area of the flow passage at the predetermined location.

While the preferred embodiment of the present invention has been shown and described, it will be understood that such is merely illustrate and that changes may be made without departing from the scope of the invention as claimed.

What is claimed is:

1. A heating apparatus for heating of a fluid comprising:
   a conduit having a fluid passage therethrough for conduction of a fluid to be heated;
   heating means in heat transfer contact with a portion of said conduit for heating the fluid being conducted therethrough;
   temperature sensing means positioned in engagement with said conduit at a predetermined location along said conduit external to said conduit for sensing the temperature of fluid to be conducted through said conduit;
   means operatively associated with said temperature sensing means for controlling operation of said heating means in response to the temperature of the fluid sensed by said temperature sensing means; and
   constricting means associated with said conduit for maintaining the fluid in said fluid passage in contact with said conduit at said predetermined location when the flow rate of said fluid through said fluid passage is below a predetermined flow rate so as to guide the fluid in said conduit in temperature sensing relationship with said temperature sensing means, said constricting means being responsive to the flow rate of fluid through said fluid passage at said predetermined location to vary the cross-sectional area of the fluid passage between a predetermined cross-section area when the flow rate of said fluid is below a predetermined flow rate and a larger cross-sectional area when the flow rate of said fluid is above said predetermined flow rate, said predetermined cross-sectional area being of a size less than the unconstricted cross-sectional area of said fluid passage in said portion of said conduit in heat tranfer contact with said heating means.

2. The heating apparatus of claim 1 wherein said conduit comprises a flexible conduit and wherein said constricting means comprises contact means engageable with said flexible conduit at said predetermined location for compressing said flexible conduit to constrict the cross-sectional area of said flow passage to said predetermined cross-sectional area when the flow rate of said fluid is below said predetermined flow rate.

3. The heating apparatus of claim 2 wherein said contact means includes at least one groove therein into which a portion of said flexible conduit at said predetermined location is forced to define said predetermined cross-sectional area of said fluid passage.

4. The heating apparatus of claim 3 wherein said contact means comprises a contact member movable between a contact position in which said contact member engages said flexible conduit to constrict the cross-sectional area of said flow passage to said predetermined cross-sectional area and a second position in which the cross-sectional area of said flow passage is larger than said predetermined cross-sectional area, and biasing means for urging said contact member towards said contact position, said contact member being movable towards said second position in response to the flow rate of the fluid in said flow passage being at a value greater than said predetermined flow rate.

5. The heating apparatus of claim 2 wherein said portion of said conduit comprises a plastic bag member having at least one flow passage therethrough through which the fluid to be heated is adapted to be conducted.

6. The heating apparatus of claim 5 wherein said temperature sensing means comprises a first temperature transmitter, and said apparatus further includes a second temperature transmitter in abutment with said conduit, and first protection means responsive to said second temperature transmitter for rendering said heating means inoperative to heat fluid conducted through said conduit when the temperature of the fluid in said conduit exceeds a first predetermined temperature established by said first temperature transmitter.

7. The heating apparatus of claim 6 further including second protection means for rendering said heating means inoperative in response to the temperature of said heating means in heat transfer contact with said portion of said conduit exceeding a second predetermined temperature higher than said first predetermined temperature.

8. The heating apparatus of claim 7 wherein said heating means comprises electrical heating members in abutment with said portion of said conduit, and wherein said second protection means comprises means for interrupting the current supply to said heating members when the temperature of said heating members exceeds said second predetermined temperature.

9. The heating apparatus of claim 1 wherein said predetermined location at which said temperature sensing means is positioned is spaced from said heating means a distance sufficient so that said temperature sensing means is substantially unaffected by the heat generated by said heating means.

10. The heating apparatus of claim 9 wherein said conduit includes an inlet end and an outlet end, wherein said heating means is in said heat transfer contact with a portion of said conduit intermediate said inlet and said outlet ends thereof, and wherein said predetermined location is adjacent one of said inlet and outlet ends of said conduit.

11. The heating apparatus of claim 10 wherein said predetermined location is adjacent said outlet end.

12. The heating apparatus of claim 1 wherein said conduit comprises a plastic bag having a first section defining a first portion of said fluid passage, and a first channel section spaced from said first section and being located at said predetermined location along said plastic bag, said first channel section defining a second portion of said fluid passage, and said plastic bag being arranged with respect to said heating means and said temperature sensing means such that said first section is in heat transfer contact with said heating means and said first channel section is in temperature sensing relationship with said temperature sensing means and is spaced from said heating means a sufficient distance to thermally insulate said first channel section from the heating effects of said heating means.

13. The heating apparatus of claim 12 wherein said plastic bag includes a second channel section in fluid communication with said first portion of said fluid passage and spaced from said first section for introducing fluid into said first portion of said fluid passage.

14. The heating apparatus of claim 13 wherein said first section comprises a plurality of longitudinally extending flow channels in side-by-side relationship to define a laterally extending heat transfer surface for arrangement in heat transfer contact with the heating means, and wherein said first and second channel sections extend laterally with respect to said laterally extending heat transfer surface.

15. A method of heating a fluid comprising the steps of:
providing a plastic bag having a first section defining at least one flow passage through which a fluid to be heated is to be conducted and a first channel section spaced from said first section and being in fluid communication with said at least one fluid passage in said first section;
arranging said plastic bag with respect to heating means for heating of a fluid being conducted through said first section of said plastic bag so that said first section is in heat transfer contact with said heating means and so that the said first channel section is spaced from said heating means;
positioning temperature sensing means in external temperature sensing relationship with said first channel section for sensing the temperature of the fluid to be conducted therethrough;
varying the cross-sectional area of said first channel section in response to the flow rate of fluid through said first channel section between a predetermined cross-sectional area when the flow rate of fluid through said first channel section is below a predetermined flow rate and a larger cross-sectional area when the flow rate of fluid is above said predetermined flow rate so as to maintain the fluid being conducted through said first channel section in contact with said first channel section of said plastic bag to thereby guide the fluid in said first channel section in temperature sensing relationship with said temperature sensing means, said predetermined cross-sectional area being of a size less than the unconstricted cross-sectional area of said at least one flow passage of said first section of said plastic bag; and
controlling said heating means in response to the temperature sensed by said temperature sensing means so as to maintain the temperature of the fluid being conducted through said plastic bag at a predetermined temperature.

16. The method of claim 15 wherein said plastic bag further includes a second channel section in fluid communication with said at least one flow passage and spaced from said first section for introducing fluid into said at least one flow passage.

17. The method of claim 16 wherein said first section of said plastic bag comprises a plurality of longitudinally extending flow channels in side-by-side relationship to define a laterally extending heat transfer surface with respect to which said heating means is arranged in heat transfer contact, and wherein said first and second channel sections extend laterally with respect to said laterally extending heat transfer surface.

* * * * *